US011679036B2

(12) United States Patent
Schiffer et al.

(10) Patent No.: US 11,679,036 B2
(45) Date of Patent: Jun. 20, 2023

(54) DETERMINING DIAPER LOADING USING COLOR DETECTION OR ACTIVITY STATE

(71) Applicant: Verily Life Sciences LLC, South San Francisco, CA (US)

(72) Inventors: Brian Schiffer, San Francisco, CA (US); Tushar Parlikar, Somerville, MA (US); Brian Ward Guilardi, San Jose, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 933 days.

(21) Appl. No.: 16/383,337

(22) Filed: Apr. 12, 2019

(65) Prior Publication Data
US 2020/0323700 A1   Oct. 15, 2020

(51) Int. Cl.
*A61F 13/42*   (2006.01)
*A61B 5/11*   (2006.01)
(Continued)

(52) U.S. Cl.
CPC ............. *A61F 13/42* (2013.01); *A61B 5/11* (2013.01); *A61B 5/6808* (2013.01);
(Continued)

(58) Field of Classification Search
CPC ............ A61F 13/42; A61F 2013/422; A61F 2013/424; A61F 2013/8491; A61B 5/11;
(Continued)

(56) References Cited

U.S. PATENT DOCUMENTS

| 3,013,257 A | 12/1961 | Carmelo |
| 3,261,987 A | 7/1966 | Chapin |

(Continued)

FOREIGN PATENT DOCUMENTS

| CN | 205246547 | 5/2016 |
| CN | 106198538 | 12/2016 |

(Continued)

OTHER PUBLICATIONS

U.S. Appl. No. 15/971,306, "Notice of Allowance", dated Oct. 22, 2019, 9 pages.
(Continued)

*Primary Examiner* — Joseph H Feild
*Assistant Examiner* — Rufus C Point
(74) *Attorney, Agent, or Firm* — Kilpatrick Townsend & Stockton LLP

(57) ABSTRACT

Systems and methods for detecting determining a volume of urine in an absorbent article such as a diaper. A diaper loading application obtains a first measurement of ambient light received from a photodetector while a light source is off and a second measurement from the photodetector while the light source is transmitting light on an absorbent article. The application determines a normalized measurement of light reflected from an absorbent article by removing an ambient light signal from the second measurement based on the first measurement. The application determines, from the normalized measurement, a presence of urine in the absorbent article. The application further determines an estimated volume of urine in the absorbent article, wherein the determining is based on an elapsed time since the presence of urine and an activity state of an infant wearing the absorbent article.

20 Claims, 10 Drawing Sheets

(51) Int. Cl.
*A61B 5/00* (2006.01)
*G06N 20/00* (2019.01)
*G01N 21/55* (2014.01)
*G01P 13/00* (2006.01)
*G01J 1/42* (2006.01)
*G01N 21/25* (2006.01)
*A61F 13/84* (2006.01)

(52) U.S. Cl.
CPC .......... *G01J 1/4204* (2013.01); *G01N 21/251* (2013.01); *G01N 21/55* (2013.01); *G01P 13/00* (2013.01); *G06N 20/00* (2019.01); *A61B 2503/04* (2013.01); *A61B 2562/0219* (2013.01); *A61F 2013/422* (2013.01); *A61F 2013/424* (2013.01); *A61F 2013/8491* (2013.01)

(58) Field of Classification Search
CPC .............. A61B 5/6808; A61B 2503/04; A61B 2562/0219; G01J 1/4204; G01N 21/251; G01N 21/55; G01N 21/78; G01N 21/80; G01N 2021/7759; G01N 2021/7796; G01N 2201/0616; G01N 2201/12707; G01P 13/00; G01P 15/18; G06N 20/00; G06N 5/003
See application file for complete search history.

(56) References Cited

U.S. PATENT DOCUMENTS

| | | | |
|---|---|---|---|
| 4,128,760 A * | 12/1978 | Del Signore, II | G01J 1/4204 356/222 |
| 4,315,159 A | 2/1982 | Niwa et al. | |
| 5,069,214 A | 12/1991 | Samaras et al. | |
| 5,079,541 A | 1/1992 | Moody | |
| 5,616,140 A | 4/1997 | Prescott et al. | |
| 5,654,803 A | 8/1997 | Howard, III et al. | |
| 6,147,592 A | 11/2000 | Ulrich et al. | |
| 6,287,253 B1 | 9/2001 | Ortega et al. | |
| 8,111,165 B2 | 2/2012 | Ortega et al. | |
| 8,416,088 B2 | 4/2013 | Ortega et al. | |
| 8,628,506 B2 | 1/2014 | Ales, III et al. | |
| 8,920,332 B2 | 12/2014 | Hong et al. | |
| 8,935,006 B2 | 1/2015 | Vu et al. | |
| 10,117,598 B1 | 11/2018 | Mouradian | |
| 11,373,102 B2 | 6/2022 | Pathak et al. | |
| 11,607,143 B2 | 3/2023 | He | |
| 2002/0124295 A1 | 9/2002 | Fenwick et al. | |
| 2004/0022053 A1 | 2/2004 | Sharon et al. | |
| 2005/0019508 A1 | 1/2005 | Engel et al. | |
| 2007/0130893 A1* | 6/2007 | Davies | A61B 5/1123 54/1 |
| 2008/0021429 A1 | 1/2008 | Klofta et al. | |
| 2008/0262381 A1 | 10/2008 | Kolen | |
| 2009/0157025 A1 | 6/2009 | Song et al. | |
| 2009/0275908 A1 | 11/2009 | Song | |
| 2010/0164733 A1 | 7/2010 | Ales et al. | |
| 2010/0185068 A1 | 7/2010 | Park et al. | |
| 2010/0241094 A1 | 9/2010 | Sherron | |
| 2010/0290948 A1 | 11/2010 | Song | |
| 2012/0116337 A1 | 5/2012 | Ales et al. | |
| 2012/0310192 A1 | 12/2012 | Suzuki et al. | |
| 2013/0001422 A1 | 1/2013 | Lavon et al. | |
| 2013/0066289 A1 | 3/2013 | Song et al. | |
| 2014/0143183 A1 | 5/2014 | Sigal et al. | |
| 2014/0200538 A1 | 7/2014 | Euliano et al. | |
| 2014/0228712 A1* | 8/2014 | Elliott | G16H 20/30 600/587 |
| 2014/0275854 A1 | 9/2014 | Venkatraman et al. | |
| 2015/0061863 A1 | 3/2015 | Barfield, Jr. et al. | |
| 2015/0150732 A1 | 6/2015 | Abir | |
| 2015/0164377 A1 | 6/2015 | Nathan et al. | |
| 2015/0272482 A1 | 10/2015 | Houmanfar et al. | |
| 2015/0288877 A1 | 10/2015 | Glazer | |
| 2015/0297125 A1 | 10/2015 | Montgomery et al. | |
| 2016/0003615 A1 | 1/2016 | Biswas et al. | |
| 2016/0120455 A1 | 5/2016 | Pop et al. | |
| 2016/0256086 A1 | 9/2016 | Byrd et al. | |
| 2016/0287074 A1* | 10/2016 | Pradeep | G09B 5/06 |
| 2016/0287076 A1 | 10/2016 | Pradeep et al. | |
| 2016/0292576 A1* | 10/2016 | Pradeep | G06N 99/00 |
| 2016/0292584 A1 | 10/2016 | Weinberg et al. | |
| 2016/0296144 A1 | 10/2016 | Gaddam et al. | |
| 2017/0049336 A1 | 2/2017 | Hatch | |
| 2017/0128274 A1 | 5/2017 | Varga et al. | |
| 2017/0172433 A1 | 6/2017 | Olivier | |
| 2017/0215808 A1 | 8/2017 | Shimoi et al. | |
| 2017/0252225 A1* | 9/2017 | Arizti | G08B 21/20 |
| 2017/0348162 A1 | 12/2017 | Arizti et al. | |
| 2017/0354547 A1 | 12/2017 | Abir | |
| 2018/0008478 A1 | 1/2018 | Xu | |
| 2018/0056128 A1 | 3/2018 | Narasimha Rao et al. | |
| 2018/0253957 A1 | 9/2018 | Jhangiani et al. | |
| 2018/0333306 A1* | 11/2018 | Ahong | A61F 13/42 |
| 2018/0353134 A1 | 12/2018 | Walter et al. | |
| 2019/0132948 A1 | 5/2019 | Longinotti-Buitoni et al. | |
| 2019/0304000 A1* | 10/2019 | Simpson | G06Q 30/0633 |
| 2019/0340515 A1 | 11/2019 | Pathak et al. | |
| 2020/0022637 A1* | 1/2020 | Kurzrock | G01N 21/4738 |
| 2020/0129380 A1 | 4/2020 | Sazonov et al. | |
| 2020/0163602 A1 | 5/2020 | Pareddy et al. | |
| 2020/0260998 A1 | 8/2020 | Auerbach et al. | |
| 2020/0323450 A1 | 10/2020 | He | |
| 2021/0100694 A1* | 4/2021 | Baek | A61F 13/42 |

FOREIGN PATENT DOCUMENTS

| | | | |
|---|---|---|---|
| EP | 2425771 | 3/2012 | |
| EP | 2832323 | 2/2015 | |
| JP | S61296239 | 12/1986 | |
| JP | 2002515975 A * | 5/2002 | A61F 13/42 |
| WO | WO-9708523 A1 * | 3/1997 | G01J 1/4204 |
| WO | 0100117 | 1/2001 | |
| WO | 02063260 | 8/2002 | |
| WO | 2007128038 | 11/2007 | |

OTHER PUBLICATIONS

Chinese Application No. 201920639694.1, "Office Action", dated Mar. 27, 2020, 3 pages.
International Application No. PCT/US2019/030691, "International Search Report and Written Opinion", dated Dec. 5, 2019, 18 pages.
U.S. Appl. No. 16/383,136, Notice of Allowance, dated Feb. 24, 2022, 9 pages.
U.S. Appl. No. 16/841,129, Non-Final Office Action, dated Feb. 17, 2022, 17 pages.
U.S. Appl. No. 15/971,306, "Non-Final Office Action", dated Jan. 28, 2019, 12 pages.
U.S. Appl. No. 16/745,771, Ex Parte Quayle Action, Jun. 29, 2020, 6 pages.
U.S. Appl. No. 16/745,771, Notice of Allowance, dated Aug. 24, 2020, 9 pages.
Chinese Application No. 201920639694.1, Notice of Decision to Grant, dated Jul. 27, 2020, 2 pages.
Chinese Application No. 201920640368.2, Notice of Decision to Grant, dated Apr. 20, 2020, 2 pages.
International Application No. PCT/US2020/027920, International Search Report and Written Opinion, dated Jul. 24, 2020, 10 pages.
U.S. Appl. No. 16/383,136, Non-Final Office Action, dated Oct. 8, 2021, 39 pages.
U.S. Appl. No. 16/949,759, Notice of Allowance, dated Nov. 24, 2021, 11 pages.
Lara et al., "A Survey on Human Activity Recognition using Wearable Sensors", IEEE Communications Surveys & Tutorials, vol. 15, Issue 3, Nov. 29, 2012, pp. 1192-1209.
Russell et al., "Artificial Intelligence: A Modern Approach", 2nd Edition, 2003, pp. 649-789.

(56) References Cited

OTHER PUBLICATIONS

U.S. Appl. No. 15/971,306, "Final Office Action", dated Aug. 8, 2019, 8 pages.
Kastle et al., "A New Family of Sensors for Pulse Oximetry", Hewlett Packard Journal, vol. 48, Article 7, Feb. 1997, pp. 1-17.
Kim et al., "Miniaturized Battery-Free Wireless Systems for Wearable Pulse Oximetryy", Advanced Functional Materials, vol. 27 No. 1, 1604373., Jan. 5, 2017, pp. 1-18.
Leonard et al., "Standard Pulse Oximeters Can be Used to Monitor Respiratory Rate", Emergency Medicine Journal, vol. 20, No. 6, Nov. 2003, pp. 524-525.
International Application No. PCT/US2019/030684, "International Search Report and Written Opinion", dated Jun. 25, 2019, 11 pages.
International Application No. PCT/US2019/030691, "Invitation to Pay and Partial International Search Report" dated Jul. 30, 2019, 13 pages.
U.S. Appl. No. 16/841,129, Notice of Allowance, dated Nov. 14, 2022, 12 pages.
Application No. EP20787437.1, Extended European Search Report, dated Nov. 30, 2022, 10 pages.
U.S. Appl. No. 16/841,129, Non-Final Office Action, dated Jul. 14, 2022, 20 pages.
Application No. EP19724681.2, Office Action, dated Jun. 9, 2022, 4 pages.

\* cited by examiner

DETERMINING DIAPER LOADING USING COLOR DETECTION OR ACTIVITY STATE

FIELD

The present application generally relates to determining a volume of bodily exudate present in an absorbent article and more specifically relates to determining a volume of urine in a diaper based on a changing color of a color changing indicator the diaper and/or a detected activity of the wearer of the diaper.

BACKGROUND

Existing solutions exist for determining a level of bodily exudate in an absorbent article are inadequate. For example, some existing solutions rely on use temperature or humidity sensors alone, which can lead to inaccurate measurements. For example, a humidity sensor may be located too far away from bodily exudate to detect a sudden increase in humidity. Or a temperature sensor may indicate an elevated temperature, but the location of sensing may not be representative of the temperature of the absorbent article overall.

Finally, other solutions for detecting a level of bodily exudate present are prone to erroneous measurements due to movement of the wearer. For example, a sensor measurement can include noise or error caused by either motion of the sensor relative to absorbent article or motion of the absorbent article itself (e.g., due to the wearer of the absorbent article moving).

Hence, new solutions are needed for at least the reasons described above.

SUMMARY

In an example, an application determines a volume of urine in an absorbent article such as a diaper. The application obtains a first measurement of ambient light received from a photodetector while a light source is off. The application obtains a second measurement from the photodetector while the light source is transmitting light on the absorbent article. The second measurement includes a measurement of the ambient light and the transmitted light reflected from an absorbent article. The application then determines a normalized measurement of light reflected from an absorbent article by removing an ambient light signal from the second measurement based on the first measurement. The application determines, from the normalized measurement, a presence of urine in the absorbent article. The application further determines a degree of fullness of the absorbent article.

In an aspect, the application determines, based on the degree of fullness, that the absorbent article should be replaced.

In an aspect, determining the degree of fullness is based on a size of the absorbent article.

In an aspect, determining the degree of fullness includes using one or more of (i) a regression model or (ii) a machine learning model to solve a function based on the elapsed time and the activity state.

In an aspect, determining the degree of fullness is based on (iii) an additional elapsed time since the absorbent article was placed on the infant.

In an aspect, the activity state includes one of (i) asleep or (ii) awake.

In an aspect, the application further includes accessing a set of demographics about the infant, and determining the degree of fullness is based in part on the demographics.

In an aspect, the application accesses a type of the absorbent article. The type is one of (i) a nighttime diaper or (ii) a daytime diaper, and determining the degree of fullness is based in part on the type.

In an aspect, determining the state of the infant includes receiving, from an movement sensor, inertial measurements in three dimensions for a time period. The determining includes calculating statistical data derived from the inertial measurements. The determining further includes providing the inertial measurements and the statistical data to a predictive model. The determining further includes receiving, from the predictive model and based on the inertial measurements, a determined activity.

In an aspect, the second measurement includes separate measurements of red light, green light, and blue light. Determining the normalized measurement of light includes determining a separate intensity of red light, green light, and blue light. Determining the degree of fullness is based on the intensities of the red, green, and blue lights.

In an aspect, the light source is configured to transmit light at a particular wavelength that is determined based on a responsiveness of the absorbent article to different wavelengths of light.

In an aspect, the absorbent article includes a printed or coated region including a color changing indicator.

In an aspect, the application further retrieves, from a memory, a stored color calibration value. The application determines, based on the normalized measurement of light and the stored color calibration value, a color of the absorbent article. The stored color calibration value is determined using a white colored object and the determining the color includes white level correction.

In a further aspect, a system for determining a volume of bodily exudate in an absorbent article includes a light source, a photodetector, a movement sensor; and a processor. The processor is configured to obtain a first measurement of ambient light received from the photodetector while the light source is off. The processor is configured to obtain a second measurement from the photodetector while the light source is transmitting light. The second measurement includes a measurement of the ambient light and the transmitted light reflected from an absorbent article. The processor is configured to determine a normalized measurement of light reflected from an absorbent article by removing an ambient light signal from the second measurement based on the first measurement of ambient light. The processor is further configured to obtain, from the movement sensor, a time series of data including an inertial measurement for each of a set of time periods. The processor is further configured to transmit, to an external device, at least one of (i) the normalized measurement of light or (ii) the time series of data. The processor is further configured to receive, from the external device, a degree of fullness of the absorbent article.

In an aspect, the transmitting causes the external device to determine the time until the absorbent article is expected to be full by using a regression model to solve a function based on an elapsed time since a detection of a presence of urine and an activity state of an infant wearing the absorbent article.

In an aspect, the transmitting causes the external device to determine the degree of fullness based on (iii) an additional elapsed time since the absorbent article was placed on an infant.

In a further aspect, a system includes a computer-readable medium storing non-transitory computer-executable instructions and a processing device communicatively coupled to the computer-readable medium for executing the non-transitory computer-executable instructions. Executing the non-transitory computer-executable instructions configures the processing device to perform operations. The operations include obtaining a first measurement of ambient light received from a photodetector while a light source is off. The operations include obtaining a second measurement from the photodetector while the light source is transmitting light. The second measurement includes a measurement of the ambient light and the transmitted light reflected from an absorbent article. The operations include determining a normalized measurement of light reflected from an absorbent article by removing an ambient light signal from the second measurement based on the first measurement of ambient light. The operations include determining, from the normalized measurement of light, a presence of urine in the absorbent article. The operations include calculating, based on one or more of (i) an elapsed time since the presence of urine and (ii) an activity state of an infant wearing the absorbent article, that the absorbent article should be replaced. The calculating is based on one or more of: an elapsed time since the absorbent article was placed on the infant and (ii) a degree of fullness of the absorbent article.

In an aspect, the calculating includes using one or more of (i) a regression model or (ii) a machine learning model to solve a function based on the elapsed time and the activity state.

In an aspect, the activity state is determined by receiving, from an movement sensor, a set of inertial measurements in three dimensions for a time period, calculating statistical data derived from the inertial measurements, providing the inertial measurements and the statistical data to a predictive model, and receiving, from the predictive model and based on the inertial measurements, a determined activity.

In an aspect, the light source is configured to transmit light at a particular wavelength that is determined based on a responsiveness of the absorbent article to different wavelengths of light.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

Features, embodiments, and advantages of the present disclosure are better understood when the following Detailed Description is read with reference to the accompanying drawings.

FIG. 4 includes FIGS. 4A and 4B, according to certain aspects of the present disclosure.

DETAILED DESCRIPTION

Aspects described herein provide solutions for accurately determining a volume of bodily exudate (e.g., urine or feces) in an absorbent article such as an infant diaper by using a color detection system in conjunction with an activity classification system. More specifically, an example color detection system uses a pulsed light source to accurately detect the color of an object such as a color changing indicator in an absorbent article (e.g., a diaper), even in the presence of ambient light. An activity classification system can determine an activity state of an infant wearing the absorbent article by analyzing measurements obtained from an inertial sensor attached to the absorbent article.

More specifically, an example color detection system includes one or more light sources such as LEDs, one or more photodetectors configured to detect light, and an electronic circuit or device such as a photometric front end or a general purpose processor configurable to receive information about detected color, filter out a contribution of the ambient light, and output a representation of the detected color. A color detection system is attached to an infant's diaper and oriented to allow the color detection system to shine light on a portion of the diaper containing a color changing indicator. A color changing indicator can change color, for example, based on the presence or absence of bodily exudate.

An example activity classification system receives measurements from a movement sensor such as an accelerometer or gyroscope. The sensor is placed on the wearer, e.g., is pinned to a diaper. By using a predictive model or state machine, the activity classification system determines whether the wearer is awake or asleep. Whether the wearer is awake or asleep, in conjunction with other data such as diaper information, improves the accuracy and reliability of detecting a presence or volume of bodily exudate such as urine. As such, disclosed systems provide advantages of systems that rely solely on detection of a color of a color changing indicator in a diaper or another sensor, thereby facilitating correction or avoidance of errors caused by movement of the sensor or the wearer of the sensor.

These illustrative examples are given to introduce the reader to the general subject matter discussed herein and the disclosure is not limited to this example. The following sections describe various additional non-limiting examples and examples of color sensing using pulsed light.

Figure 1:
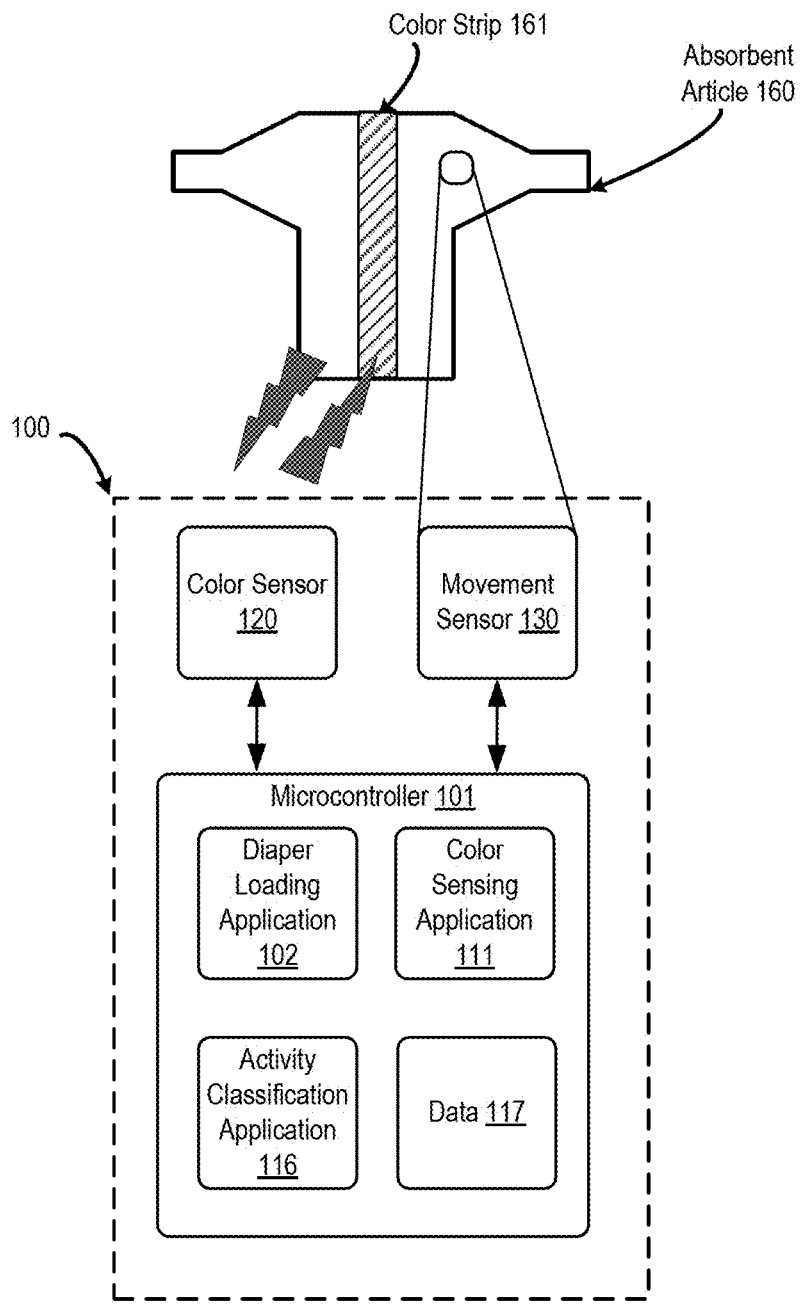
FIG. 1 depicts a block diagram of an example of an infant sensing system, according to certain aspects of the present disclosure.

FIG. 1 depicts a block diagram of an example of an infant sensing system, according to certain aspects of the present disclosure. FIG. 1 depicts infant sensing system 100, which includes color sensor 120, movement sensor 130, and microcontroller 101. Microcontroller 101 includes diaper loading application 102, color sensing application 111, activity classification application 116, and data 117. Data 117 can include demographic data (sex, age, weight, etc.), data about the material qualities of an absorbent article, an activity state of an infant, and so on. Data 117 can be input via a user interface, e.g., from a caregiver, or downloaded from an external device.

In an example, diaper loading application 102 operates in conjunction with color sensing application 111 and activity classification application 116 to determine a volume of bodily exudate such as urine in absorbent article 160. As explained further herein, absorbent article 160 can include a color strip 161 that responds to a presence or amount of urine. Color sensing application 111 determines a change in color in color strip 161 and determines a presence of urine in absorbent article 160. In another example, color sensing application 111 can also be used to detect the color of any other object such as a color changing indicator that changes color based on the presence of another chemical.

Activity classification application 116 can determine a state of an infant wearing absorbent article 160. Movement sensor 130, which can be an accelerometer, gyroscope, or other sensor type, can be placed or adhered to absorbent article 160. Activity classification application 116 can determine a state of an infant such as whether the infant is asleep, awake, resting, and so on.

In an example, the movement sensor 130 is attached to an infant's clothing or absorbent article 160. The movement sensor 130, which can include an accelerometer or a gyroscope, provides measurements. Activity classification application 116 can receive the measurements from the movement sensor 130 and use a predictive model such as a machine learning model, state-flow-model, or algorithm to determine activities performed by the infant wearing the movement sensor. In an example, the predictive model is trained to determine, based on the infant's movement, an activity that the infant is performing such as sleep or sitting up. The activity classification system can then indicate to an operator of the monitor the predicted activity of the infant, for example that the baby is in a deep sleep. Examples of suitable processes for activity classification are described with respect to FIGS. 7 and 8.

In conjunction with an indication of a presence of urine from color sensing application 111 and a predicted activity state from activity classification application 116, diaper loading application 102 can determine a volume of urine present in absorbent article 160. A volume of urine can be referred to as a diaper load. In some cases, statistical approaches can be used. Different factors can be used such as an elapsed time since a first urination event, a diaper size, or the state of an infant. An example of a process used to determine a volume of urine in an absorbent article is described with respect to FIG. 9.

Infant sensing system 100 can be implemented on a slim material such as plastic or flexible substrate. For example, infant sensing system 100 can be 1-2 centimeters wide and 2-5 millimeters thick. Infant sensing system 100 can be made sufficiently small and thin to be placed in an absorbent article such as a diaper, as discussed with respect to FIG. 3. In an example, infant sensing system 100 can be placed in a diaper that includes a color changing indicator such that a light source and a photodetector are aligned with the color changing indicator.

In an example, operations performed by microcontroller 110 can be performed by an external device. Examples include a monitor connected by a local radio connection (e.g., WiFi or Bluetooth) and a remote server that connected to microcontroller 101 via the internet. For example, diaper loading application 101, color sensing application 111, and/or activity classification application 116 can delegate some or all of the operations described herein to an external device. Advantages include, but are not limited to, reducing battery life of infant sensing system 100, or improved performance due to availability of additional data sets, e.g., training data, or processing power on the external device.

Any or all of the processes described herein, for example those discussed with respect to FIGS. 6-9 can be performed by the external device. For example, microcontroller 101 transmits data such as measured color from color sensor 120 or movement data from movement sensor 130 to the external device. In turn, the external device processes the operations to determine a significance of the detected color or movements.

Figure 2:
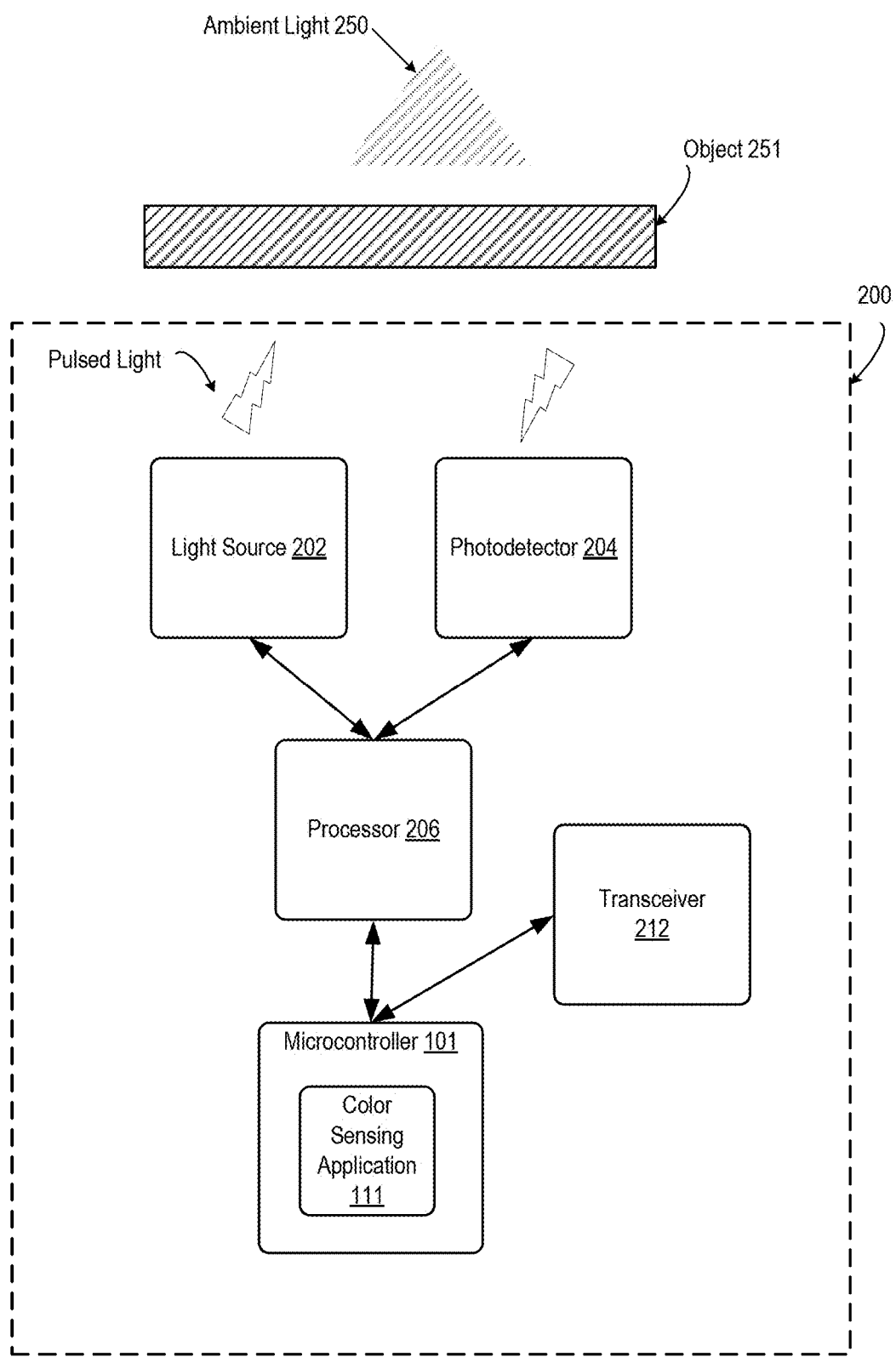
FIG. 2 depicts a block diagram of an example of a color detection system, according to certain aspects of the present disclosure.

FIG. 2 depicts a block diagram of an example of a color sensing system, according to certain aspects of the present disclosure. FIG. 2 includes color sensing system 200, which includes light source 202, photodetector 204, processor 206, and microcontroller 101. Microcontroller 101 can implement the functionality of color sensing system 200, infant sensing system 100, or both. Further, for example purposes, microcontroller 101 is depicted in color sensing system 200, but a different microcontroller, microprocessor, or other processor can be used. In an aspect, only one of the processor 206 and the microcontroller 101 is present.

Color sensing system 200 can be configured to measure a color of an object 251 (e.g., an absorbent article or a color strip in an absorbent article), including in the presence of ambient light 250, to determine a loading of an absorbent article.

Figure 10:
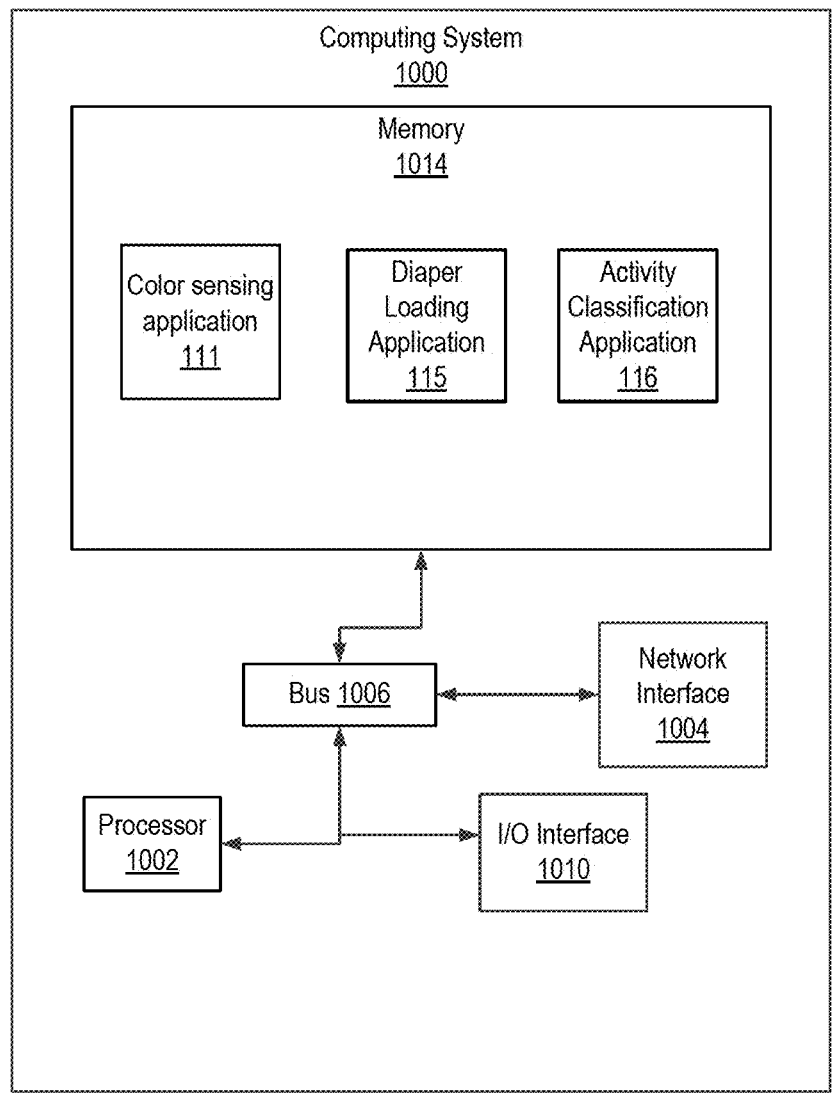
FIG. 10 is a diagram depicting an example computing system for performing functions related to color detection and detection of bodily exudate, according to some aspects of the present disclosure.

Color sensing system 200 also includes a microcontroller 101. Microcontroller 101 can be any controller, processor, application specific integrated circuit or other processing device. An example of a computing device is shown in FIG. 10. Microcontroller 101101 can execute color sensing application 111 as well as other processor-executable instructions to perform aspects of the present disclosure.

The functions of microcontroller 101101 can be implemented by processor 206 or vice versa. Microcontroller 101101 can store data 117, which can include a state of an infant, demographic information about an infant, information about a particular absorbent article worn by an infant, and so forth.

Ambient light 250 can be any kind of light present in an environment that is not generated by light source 202, which can include light from natural sources, e.g., sunlight, or artificial light such as light created via incandescent light sources, halogen light sources, light emitting diode ("LED") light sources, fluorescent light sources, laser sources, etc. Even though ambient light can have different color spectra depending on the ambient light source(s) present, infant sensing system 100 can electronically remove the contribution of such ambient light to light detected by the photodetector and accurately detect the color of object 251 based on reflected light from the light source 202.

Light source 202 includes one or more light sources operable to shine light on object 251. The light sources can be any suitable artificial light source according to this disclosure, including LEDs, incandescent light sources, or other light sources. Multiple discrete light sources can be implemented individually or via an integrated package that combines multiple individual light sources into a single light source.

Light from light source 202 can be generated at one or more specific wavelengths, or can encompass multiple wavelengths. In an example, light source 202 has three sources of light: red light at wavelength 623 nanometers ("nm"), green light at wavelength 523 nm, and blue light at 455 nm wavelength. Other wavelengths of light may be employed according to different examples, depending on the application, the expected color range of a target object or color changing indicator such as a strip of litmus paper, expected ambient light spectra, or any other suitable factor. In some examples, the light source may be tunable to allow selection of a wavelength or wavelengths of light having a small contribution to the ambient light. For example, if ambient light detected by the photodetector indicates a local or global minimum magnitude at a first wavelength, the infant sensing system 100 can tune the light source 202 to emit light substantially at the first wavelength.

In this example, the color detection system pulses the light emitted by light source 202 by activating for a short duration, e.g., 1-5 microseconds to 500 milliseconds, called a "pulse width," and then deactivating the light source. Any suitable pulse width may be employed for a particular application. Light source 202 can create a separate pulse for red, blue, and green, and output the corresponding values. For example, a pulse width of 5 microseconds may be advantageous to detect a color of a color changing indicator. Short pulse widths enable the infant sensing system 100 to pulse and detect different colors of light, e.g., red, green, and blue, in quick succession of each other.

The use of pulsed light enables color sensing system 200 to disambiguate the type of light reflected by the object. Specifically, color sensing system 200 can detect and filter the ambient light from detected light that includes light pulsed from the light source 202. In some examples, the color sensing system 200 can pulse the light source 202 at regular intervals, e.g., every ten minutes, or in response to an event, such as a user pressing a button on the color detection system or a humidity sensor detecting a humidity level exceeding a threshold. Additionally, the use of pulsed light as compared to constant light can lower the power consumption of color sensing system 200, thereby increasing the amount of time that the color sensing system 200 can operate from a battery.

When the light source 202 is pulsed, the detected light at photodetector 204 may be a combination of ambient light 250 and light from the pulsed light source 202 reflected from the object 251. When the light source 202 is inactive, the light detected by the photodetector 204 is ambient light. By pulsing the light source 202, color sensing system 200 is able to first obtain baseline information about the ambient light spectrum to enable the color detection system to filter light received when the light source 202 is active. Pulsing also allows the infant sensing system 100 to save power by deactivating the light source 202 when a color measurement is not being taken.

Photodetector 204 receives a light, including light reflected from the object 251, whether ambient light or light emitted by the light source 202, and generates sensor signals based on that received light. Photodetector 204 can be any device that can detect and measure light such as a photodiode, phototransistor, complementary metal-oxide-semiconductor (CMOS) image sensor, charge-coupled device (CCD) sensor, or a photo-resistor.

Photodetector 204 can detect a wide spectrum of light and output information that indicates the detected light. For example, photodetector 204 can create an electrical output that is proportional to the wavelength of the received light. Photodetector 204 can provide three outputs of an RGB triplet, e.g., a value that corresponds to red, another value for green, and another value for blue.

More specifically, the values of the triplet correspond to the amplitude of light at a range of wavelengths corresponding to a particular color. Therefore, a first value is proportional to an amplitude of red in the received light, a second value is proportional to an amplitude of green in the received light, and a third value is proportional to an amplitude of blue in the received light.

In an aspect, a photodetector 204 can be an array of individual photodetectors. Each photodetector can be configured to measure a color of light. For example, one photodetector measures red, a second photodetector measures blue, and a third photodetector measures green.

Processor 206 is an electronic circuit or device such as a general-purpose processor. Processor 206 can operate in the analog domain, digital domain, or both. Processor 206 can discern the true color of the object 251 independent of any ambient light. Processor 206 receives a first output from photodetector 204 that represents the ambient light, for example, an output gathered when the light source 202 is off. Processor 206 receives a second output from photodetector 204 when the light source 202 is pulsed. Processor 206 discerns a difference between the first output and the second output and thereby isolates the color of the object, specifically the color of the reflected light on the object from the pulsed light.

In an aspect, processor 206 receives a level indicating an intensity of broad spectrum light that represents the ambient light, i.e., the point in time that the light source 202 is off, and a level indicating the intensity of for a second point in time at which one of the three colors red, blue, and green, is pulsed. Processor 206 can then disambiguate the contribution of the single pulsed color from the ambient light by comparing the intensity of the ambient light and the intensity with the single pulsed color.

Processor 206 receives a first set red, green, and blue levels from photodetector 204 for a point in time that the light source 202 is off and a second set of red, green, and blue levels from a second point in time that the light source 202 is pulsed. Processor 206 calculates a difference between the level of red between the first and second points in time, thereby calculating a contribution of red, green, and blue levels from the pulsed light.

Processor 206 may be a specialized photometric front end such as Analog Devices® ADPD105, ADPD106, or ADPD107. Processor 206 may be configured to activate light source 202 and measure a signal received by photodetector 204. For example, processor 206 can receive an analog input from photodetector 204, convert the analog input to a digital output by using a analog-to-digital converter (ADC), then store a numerical value indicating the detected color in an internal memory for later comparison with another value.

In this manner, processor 206 may be configured to disambiguate the contribution of the ambient light 250 in the analog domain and output an analog signal or digital value indicative of the color of object 251. For example, the processor 206 can provide an output, such as an RGB triplet value representing the color of object 251.

In an aspect, processor 206 can have multiple detection channels, each corresponding to a pair that of a light source 202 and a photodetector 204. As described further with respect to FIGS. 4A and 4B, each channel can be dedicated to a specific light source-photodetector pair, or a "cell." Each cell can be physically separated so that the processor 206 may measure color in multiple places. Processor 206 can also pulse the light from a particular cell differently from a light from another cell.

Color sensing application 111 can provide additional functionality such as calibration or white balancing for the signal received from light source 202. For example, microcontroller 101 receives a digital input indicating the color of the received light from processor 206. The digital input can include red, green, and blue levels. Color sensing application 111 can convert the red, green, and blue levels to hue, saturation, and lightness/value and perform calculations on the hue, saturation, and lightness/value.

Color sensing application 111 may also calibrate the received color value. For example, color sensing application 111 can retrieve known values such as the detected values when a known color, e.g. represented by a white or gray card or object that is presented to photodetector 204. Color sensing application 111 can adjust the received red, blue, and green levels according to the known calibration values.

In an aspect, microcontroller 101 may be connected to a transceiver 212. Transceiver 212 may communicate according to any suitable wireless protocol, such as Bluetooth, WiFi, near-field communication, etc. Using transceiver 212, microcontroller 101 may transmit the color of the object 251 or, if detecting bodily exudate in an absorbent article, notify an external device that an absorbent article has been soiled. Microcontroller 101 may transmit information to a remote device, such as a smartphone, smartwatch, or other wearable device, or a remote computer, such as a server, e.g., a cloud-based server, for further processing and analysis.

Microcontroller 101 can, via the transceiver 212, transmit the detected color from processor 206 to a remote server, which can map values that represent an expected reflected color from an object to a predicted volume of bodily exudate present in an absorbent article. Such a mapping can be accomplished via a table. For example, a table can contain a mapping between a Red-Blue-Green (RGB) triplet or range of triplets to a predicted volume of bodily exudate.

Object 251 can be a color changing indicator or other material that changes color based on the presence of a chemical. In an aspect, s color changing indicator can dissolve in the presence of a liquid such as urine. Accordingly, infant sensing system 100 can detect a change in color, an appearance of color, or a disappearance of color.

For example and as discussed further with respect to FIGS. 3-6, in one application, infant sensing system 100 is used to measure the presence of bodily exudate by reading a color changing indicator that changes color based on a presence or volume of a liquid. Exemplary color changing indicators include a pH strip or litmus paper strip that changes color based on detected pH level. Color sensing system 200 pulses light onto the color changing indicator and determines the amount of the pulsed light that is reflected.

More specifically, microcontroller 101 is programmed with data points from one or more wavelength-absorbance curves that correspond to different levels of acidity or pH level. By matching an absorbance level of a particular wavelength of light to a particular level of acidity, microcontroller 101 can determine a volume of a particular liquid, e.g., bodily exudate, or a specific pH level. For example, for a wavelength of light of 440 nm, if the measured absorbance is 0.1, then microcontroller 101 determines that a liquid present is basic, and is present in a low volume. In another example, if a measured absorbance of the 440 nm light is 0.3, then microcontroller determines that the liquid is present in high volume due to a high level of acidity. In this manner, microcontroller 101 need not calculate an intermediate pH level, but rather, can map absorbance or reflectance directly to volume of bodily exudate. Microcontroller 101 can determine expected reflectance, i.e., the amount of light at a particular frequency that is expected to be measured by the photodetector 204, based on an absorbance for that frequency.

The microcontroller 101 can retrieve stored calibration values from memory and determine, from the color and the calibration values, the amount of bodily exudate present in the absorbent article. For example, microcontroller 101 can store a table which maps a given value or range of color to a corresponding amount, or volume of bodily exudate present. Microcontroller 101 can have multiple tables, for example, one for each of a set of different color changing indicators. Additionally, the table can be updated, for example, in the event that a different color changing indicator is to be used.

The wavelength of light source 202 may be altered based on a particular application or color changing indicator. For example, a pH color changing indicator may have a greater response at specific wavelengths, and so the light source 202 may be selected or tuned to emit light at such wavelengths. In this manner, by using light sources with particular wavelengths that are better reflected by the color changing indicator, the system can receive stronger reflected pulsed light signals from the object. This can allow the system to more accurately determine the color of the object and therefore more accurately determine a pH value or a corresponding volume based on the determined color. Such accuracy can be particularly valuable when the color values of the color changing indicator do not change linearly with changes in pH.

Figure 3:
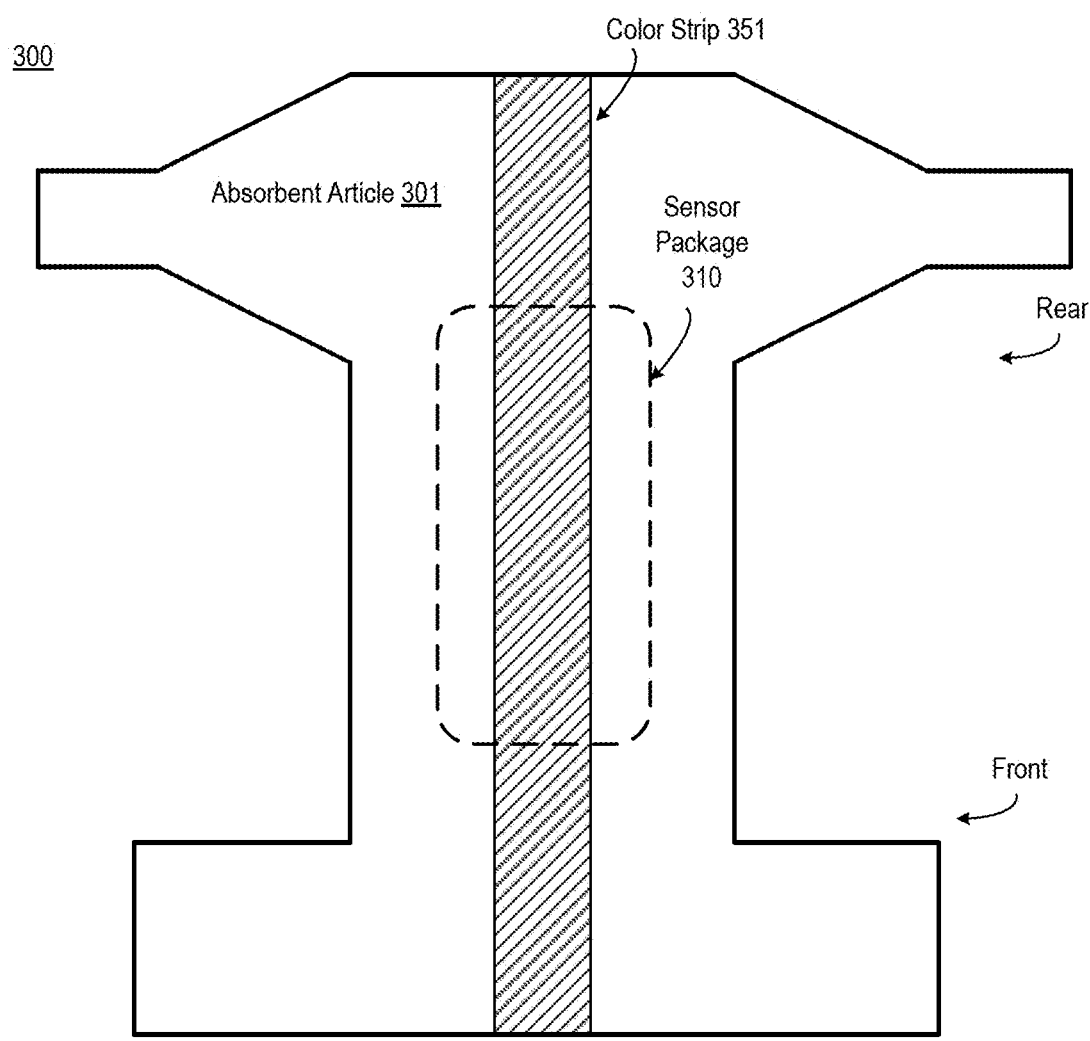
FIG. 3 depicts an absorbent article with color changing indicator and sensing device, according to certain aspects of the present disclosure.

FIG. 3 depicts an absorbent article with a pH-sensitive color changing indicator and a sensing device, according to certain aspects of the present disclosure. FIG. 3 depicts absorbent article system 300, which includes an absorbent article 301, sensor package 310, and color strip 351. In this example, the infant sensing system 100 of FIG. 1 is implemented on sensor package 310. Further, in some examples, multiple color detection systems, or multiple light sources and photodetectors for a single multiple color detection system, may be employed at different locations within the absorbent article to better detect the presence of bodily exudate at multiple different locations within the absorbent article.

Color strip 351 is shown as extending down the middle of the absorbent article from one end, shown with straps, to the other. Because bodily exudate can be non-uniformly distributed within an absorbent article, placing the color strip 351 down the middle of the absorbent article increases the chance that the color strip 351 will detect bodily exudate in the absorbent article 301. But color strip 351 can be located in different areas of the absorbent article 301. For example, color strip 351 could be located at the front of the absorbent article, or at an edge of absorbent article 301, or any combination of these or other locations.

As can be seen, sensor package 310 is aligned with color strip 351 such that the light source and photodetector elements are positioned over the color strip 351. In some examples, sensor package 310 can be removable from the absorbent article 301. For example, the sensor package 310 can be adhered to the absorbent article 301 to prevent the sensor package 310 slipping, while allowing its removal.

Absorbent article 301 can be any suitable absorbent article such as a common disposable diaper, a reusable cloth diaper, pantiliner, adult diaper, etc. Color strip 351 is a color changing indicator that is designed to change color in response to contact with a substance having a particular property, such as a pH level. For example, color strip 351 can be Bromocresol green, which changes color based on the pH of a liquid to which the color changing indicator has been exposed. The color of the Bromocresol green strip changes with the pH of bodily exudate detected. Other color changing indicators can be used. The detected pH level can be correlated with a volume of bodily exudate, because the pH level changes as the volume of bodily exudate in the absorbent article changes. Accordingly, a lookup table or function may be used to determine a volume for a given pH level, or color of the color changing indicator.

Sensor package 310 can include the infant sensing system 100 and/or the color sensing system 200, can be included within a flexible, impermeable package. For example, sensor package 310 has a housing that can withstand bodily exudate and feces, and is sufficiently thin as to not cause discomfort to a wearer of the absorbent article. Sensor package 310 may be fabricated with flexible substrate such as a thin plastic, fluoroelastomer, or tpsiv.

Sensor package 310 can be placed in the absorbent article in various different ways. In an aspect, sensor package 310 may be removed and inserted in a new absorbent article. Sensor package 310 can be covered with a material or pouch that is washable or can be wiped. For example, sensor package 310 can be inserted into an absorbent article or adhered to the inside of the absorbent article. Sensor package 310 can also be inserted into a pocket or pouch inside the absorbent article. Such a pocket or pouch can be hermetically sealed, for example, in transparent plastic that allows light to pass through. Sensor package 310 can also be permanently attached into an absorbent article and discarded after a one-time use. Sensor package 310 can also be adhered to the outside of the absorbent article via velcro or similar material.

Figure 4A:
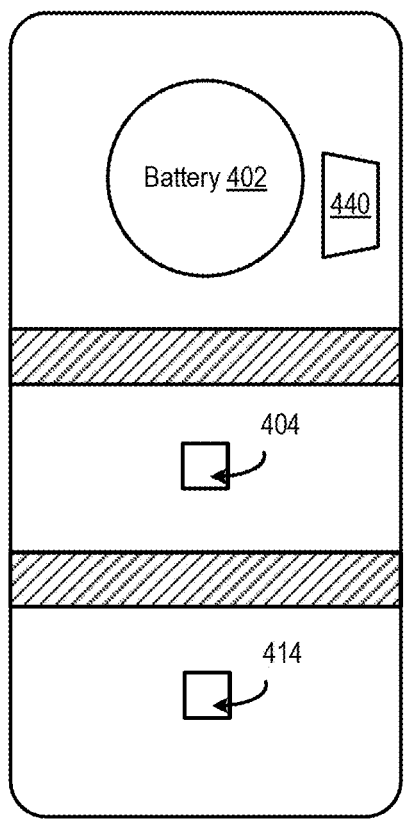
FIG. 4A represents a top side view of an example of a sensor layout for sensor package 400.
Figure 4B:
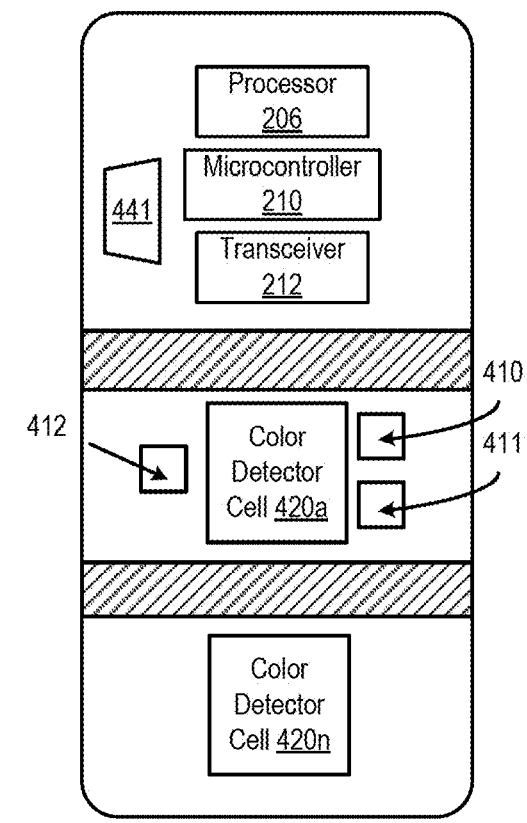
FIG. 4B represents a bottom side view of an example of a sensor layout for sensor package 400.

FIGS. 4A and 4B depict an example layout of a sensor system that can be placed in or on the outer surface of an absorbent article, according to certain aspects of the present disclosure. FIG. 4A represents a top-down view of an example of a sensor layout for sensor package 400. FIG. 4B represents a bottom-up view of an example of a sensor layout for sensor package 400. Sensor package 400 can be used in conjunction with the absorbent article 301 depicted in FIG. 3.

As depicted, the bottom is the side that is positioned to face and align with the color strip 351. The sensor system shown in FIG. 4, when placed in an absorbent article, by detecting a color of a color changing indicator in the absorbent article, can determine a presence and volume of bodily exudate present in the absorbent article in conjunction with an internal system such as microcontroller 101 that can map color to bodily exudate volume.

Sensor package 400 includes a battery 402 and one or more color detector cells 520a-n. Sensor package 400 may also include a switch 404, two electrical connectors 440-441, a volatile organic compound ("VOC") sensor 410, a temperature sensor 411, a humidity sensor 412, an additional ambient light sensor 414, processor 206, microcontroller 101, or transceiver 212. Additional ambient light sensor 414 can be used in conjunction with the photodetectors to improve or augment the light detecting capability of sensor package 400. Some aspects may not include all of the components described above, or include variants thereof.

In addition, the sensor package 400 can cause an alarm, such as an audible beep, based on a threshold level of bodily exudate being detected. Accordingly, sensor package 400 can include a speaker or other audio output device. Sensor package 400 can also cause a transmission of an alert to another device, for example, operated by a caretaker. In another aspect, sensor package 400 can transmit an alert to another device. Sensor package 400 can include a transmitter or transceiver capable of transmitting a radio signal to an external device. Color sensing application 111 operating on microcontroller 101 can also log events, such as when bodily exudate is detected, to memory for later transmission to a caregiver.

Sensor package 400 can include one or more color detector cells 420a-n. For example, multiple color detector cells 420a-n can increase the ability of the sensor package 400 to detect changes in bodily exudate across the absorbent article. Because bodily exudate may not be distributed uniformly in an absorbent article, the color of color strip 351 may not change uniformly along the length of the color changing indicator. Additionally, the presence of multiple color detector cells 420a-n enables a calculation of multiple data points to more accurately estimate the total load.

Each color detector cell 420a-n includes a light source such as an LED and a photodetector such as a photodiode. In some aspects, as discussed further with respect to FIG. 4, a color detector cell may include multiple light sources or multiple photodetectors. Each color detector cell 420a-n detects light reflected by object 251 such as a color strip 351, such as ambient light or pulsed light from the light source(s). The output of each color detector cell 420a-n is provided to a processor 206. The output of processor 206 can be provided to microcontroller 101. In some examples, each color detector cell 420a-n may have a dedicated processor 206, while in some examples, multiple color detector cells 420a-n may be connected to a common processor.

Sensor package 400 can include a switch 404 to activate or deactivate the sensor package 400. The switch 404 can be any suitable switch, such as a rocker-style on/off switch that connects the battery 402 to the electronics in sensor package 400 such as the color detector cells 520a-n and sensors 410-414. Switch 404 can also be a pushbutton switch that activates power from battery 402 to sensor package 400 for a period of time. Sensor package 400 can be configured to automatically turn off to save battery power. In an aspect, in conjunction with microcontroller 101, sensor package can be activated remotely. For example, a user can prompt an external device with a voice command, which causes the external device to transmit a request for a status of the absorbent article to the microcontroller 101 via a wireless connection, or a request to turn on or turn off the sensor package 400.

Sensor package 400 can include one or more electrical connectors such as electrical connectors 440-441. Electrical connectors 440 and 441 can be used to debug the sensor package 400, calibrate the sensor package 400, reset the sensor package 400 to factory settings, upgrade software on the sensor package 400, etc.

As discussed with respect to FIG. 1, processor 206 can discern a color of an object such as a color changing indicator. Microcontroller 101 can execute an application such as color sensing application 111 that can perform calibration of the detected color value. Transceiver 212 can notify an external device if the sensor package 400 detects the presence of bodily exudate in an absorbent article.

In an aspect, sensor package 400 can also include a VOC sensor 410. VOC sensor 410 can detect the presence of volatile organic compounds such as feces from a bowl movement or VOCs present in blood. In conjunction with data obtained from color detector cells 520a-n, the VOC sensor 410 can provide additional information to microcontroller 101 based on one or more detected volatile organic compounds.

In an aspect, sensor package 400 can also include a temperature sensor 411. Temperature sensor 411 can detect heat from substances such as bodily exudate. In conjunction with data obtained from color detector cells 520a-n, the temperature sensor 411 can provide additional information such as a temporary increase in temperature to microcontroller 101. Because a notification of a temporary increase in temperature can indicate a presence of bodily exudate, such information can improve the accuracy and reliability of the detection.

In another aspect, sensor package 400 can also include a humidity sensor 412. Humidity sensor 412 can detect the presence of humidity, e.g., from bodily exudate. In conjunction with data obtained from color detector cells 520a-n, humidity sensor 412 can provide additional information such as a notification of a temporary increase in humidity to microcontroller 101. Because a temporary increase in temperature can indicate a presence of bodily exudate, such information can improve the accuracy and reliability of the detection.

In a further aspect, sensor package 400 can also include additional ambient light sensor 414. Additional ambient light sensor 414 can be placed, as shown, oriented away from the color detector cells 420a-n to more accurately detect the ambient light. In conjunction with data obtained from color detector cells 420a-n, additional ambient light sensor 414 can provide additional information to microcontroller 101 that allows microcontroller 101 to better disambiguate the contribution of ambient light to the color of the color changing indicator. Additional ambient light sensor 414 can also provide the microcontroller 101 with information as to whether an infant who is wearing an absorbent article in which the sensor package 400 is placed is in a dark room. For example, sensor package 400 can provide an indication or a notification to a caregiver that the light in a baby's room is either on or off.

As discussed, sensor package 400 can include multiple color detector cells 420a-n. The presence of more than one color detector cell 420a-n allows for increased accuracy and reliability. For example, one color detector cell 420a-n could become obstructed by an object, rendering detected values from that cell unusable, or because bodily exudate may not be evenly distributed in an absorbent article, and therefore not evenly distributed on a color changing indicator, the use of more than one of color detector cell 420a-n increases the probability that one of the color detector cells 420a-n detects bodily exudate. In this manner, additional color detector cells 420a-n help add robustness in the case that any one of color detector cell 420a-n fails or is misaligned. Further, the additional of more sells 420a-n can provide additional local information that may help estimate total load. In contrast, fewer color detector cells 420a-n can simplify the overall system architecture and may also lower power consumption.

In another example, in a system with three detector cells 420a-c, if one detector cell 420a returns a color measurement that is inconsistent with detector cells 420b and 420c, then microcontroller 101 can ignore the measurements from detector cell 420a.

Figure 5:
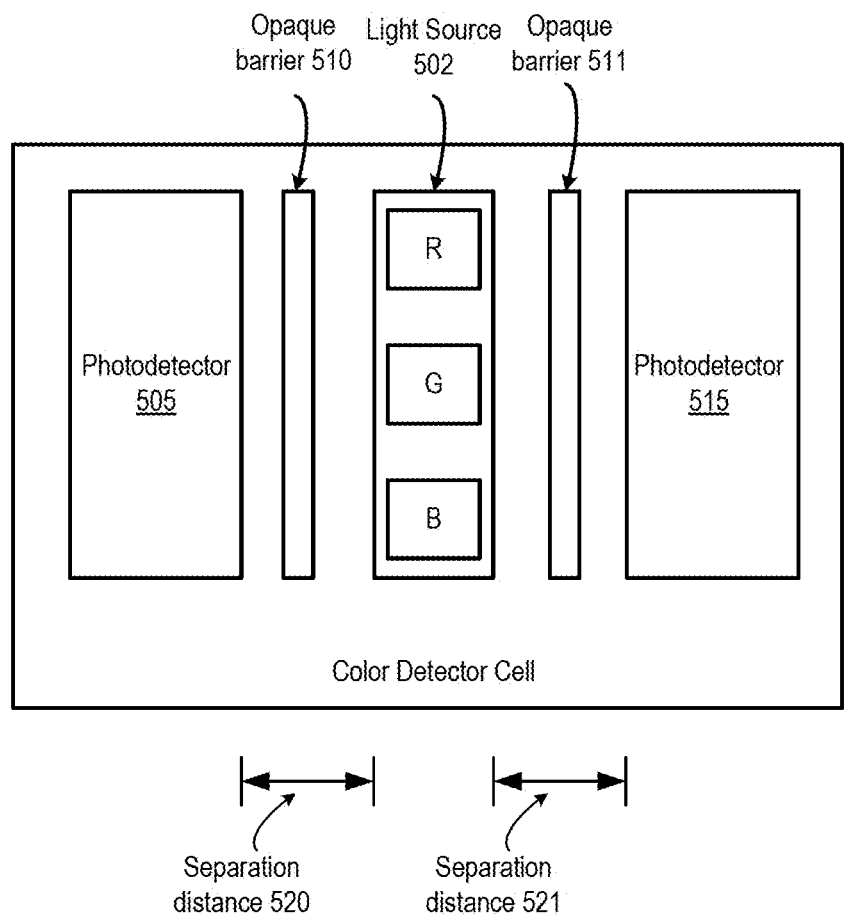
FIG. 5 depicts an example color detector cell configuration, according to certain aspects of the present disclosure.

FIG. 5 depicts an example color detector cell configuration, according to certain aspects of the current disclosure. As discussed, a sensor system such as sensor package 400 includes one or more color detection cells 520a-n. FIG. 5 shows an color detector cell 500 in more detail.

Color detector cell 500 includes two photodetectors, photodetector 505 and photodetector 515, light source 502, opaque barrier 510, and opaque barrier 511. Light source 502 can be any suitable light source according to this disclosure. As shown, light source 502 includes a red, a blue, and a green light source, though different numbers and types of light sources 502 may be used according to different examples, which can allow the light sources can be turned on and off, i.e., pulsed, separately. Pulsing the light sources 502 that emit different colors separately allows color detector cell 500 to tailor the light output to a specific wavelength of light. For example, a particular color changing indicator may be more responsive to a specific wavelength of light at a specific pH level.

Photodetectors 505 and 515 can be any suitable photodetector according to this disclosure. Photodetectors 505 and 515 are connected to the processor 206. A separation distance 520 between the light source 502 and the photodetector 505 and separation distance 521 between light source 502 and photodetector 515 can be adjusted based on the application. In particular, the closer the light source 502 and a photodetector 505 or 515 are together, the greater the portion of light received at the photodetectors from the light source 502 (and less from ambient light 250). As an example only, separation distance 520 and separation distance 521 can be adjusted from 0.1 mm to 2 mm in separation. Other distances and configurations are possible. As a distance increases, all else being equal, the intensity of the light from the light source received at the photodetector decreases. Additionally, as the distance increases, the focal area being measured increases. As the distance decreases, the sensor is more focused on a smaller area directly under the sensor.

As shown, two photodetectors 505 and 515 are used. Photodetectors 505 and 515 can be positioned to be parallel to each other. In this configuration, the combination of photodetectors 505 and 515 provides a stronger output signal to the processor 206 than otherwise. Using more than one photodetector also provides an advantage in that error can be reduced if the sensor system is misaligned with respect to the object, e.g., color strip 351.

Color detector cell 500 can include one or more opaque barriers 510-511 positioned between the light source 502 and the photodetectors 505, 515. The opaque barriers 510-511 reduce the amount of light from light source 502 that travels directly to the photodetector 505 without reflecting off of the object. Opaque barriers 510-511 can be poron or similar material. In an aspect, the photodetectors 505 or 515 can include such an opaque barrier, or an opaque housing of the photodetector 505 or 515 can be extruded in such a manner that the opaque housing is located between the LED and photodiodes. In an aspect, the opaque barriers 510-511 are omitted to simplify the design.

Figure 6:
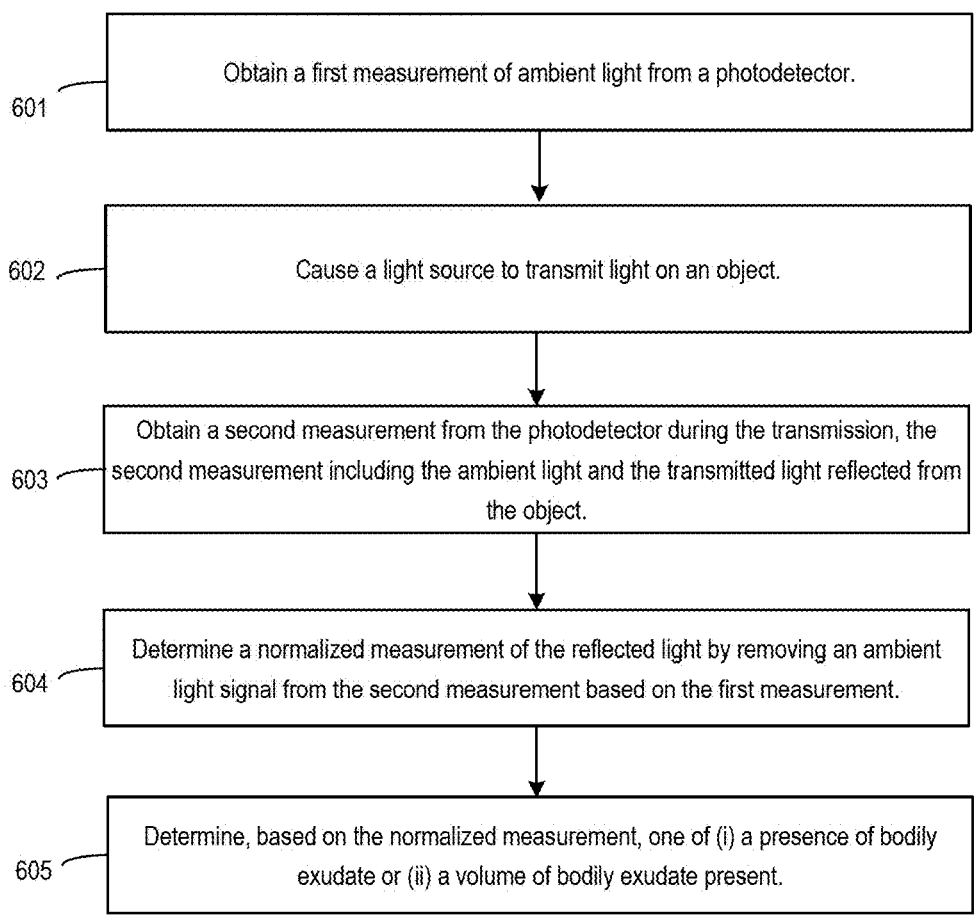
FIG. 6 is a flowchart that describes a method of detecting of color, according to certain aspects of the present disclosure.

FIG. 6 is a flowchart that describes a method of detecting color, according to certain aspects of the present disclosure. The example method of FIG. 6 will be described with respect to the color sensing application 111 of FIG. 1 or 2; however, any suitable color detection system according to this disclosure may be employed according to different examples. Further, the operations described with respect to FIG. 6 can be performed by an external device such as a monitor device connected to infant sensing system 100 via a wireless or an external server.

At block 601 of method 600, color sensing application 111 obtains a first measurement of ambient light received from the photodetector. Photodetector 204 detects the ambient light present and outputs a representation of the color of the light or a representation of an intensity of broad-spectrum light that is present. For example, photodetector 204 can create an electrical output that is proportional to the wavelength or the intensity of the received light. In an aspect, the photodetector 204 can provide three outputs that each correspond to red, green, or blue: a first that is proportional to an amplitude of red in the received light, a second that is proportional to an amplitude of green in the received light, a third that is proportional to an amplitude of blue in the received light.

Photodetector 204 provides the first measurement of light to the processor 206. In this example, the first light measurement is taken while a light source 202 is off and represents ambient light reflected from the object 251. The first light measurement can represent an intensity of broadspectrum light.

The steps of method 600 can be performed by sensor package 400 of FIG. 4 placed in an absorbent article as described with respect to FIG. 3. Because sensor package 400 can include one or more color detector cells 520a-n, in an aspect in which more than one color detector cell 520a-n are present, sensor package 400 can measure a level of ambient light at multiple photodetectors. The photodetector in each color detector cell 520a-n can independently perform the steps 601-605.

At block 602 of method 600, the color sensing application 111 causes the light source to transmit of light on an object. More specifically, processor 206 activates light source 202 for a predetermined pulse time interval. In this example, the infant sensing system 100 only includes one light source 202. But in some examples, multiple light sources may be pulsed simultaneously or individually. For example, aspects using sensor package 400 may include more than one color detector cell 520a-n. The light source in each color detector cell 520a-n may be pulsed separately or together with the other light sources.

At block 603 of method 600, the color sensing application 111 obtains a second measurement from the photodetector during the transmission, the second measurement including the ambient light and the transmitted light reflected from the object. Processor 206 obtains a second measurement of light during the time interval that the pulse from light source 202 is on. The second measurement includes the ambient light and the light from the pulsed light source 202. In an aspect such as sensor package 400, the photodetector in each color detector cell 520a-n each obtains a second measurement of light. Color sensing application 111 uses the first and second measurements to determine the color of an object.

In an aspect, color sensing application 111 can obtain more than one measurement with the ambient light and the pulsed light present. Processor 206 can average the multiple measurements together to form one single measurement that can be used as a second measurement.

At block 604 of method 600, color sensing application 111 determines a normalized measurement of the reflected light by removing an ambient light signal from the second measurement based on the first measurement. Removal can be performed in the analog domain or the digital domain.

For example, processor 206 can remove the first measurement of light from the second measurement of light by filtering in the analog domain. For example, the processor 206 subtracts the first measurement, representing the ambient light, from the second measurement, representing the ambient light combined with the reflected light from light source 202. The result of the subtraction is the light reflected from the object 251, such as a color changing indicator.

Processor 206 can operate in the digital domain. For example, processor 206 converts the first measurement into a digital or numeric representation of the red, green, and blue levels. Processor 206 converts the second measurement into a digital or numeric representation of the red, green, and blue levels. Processor 206 computes a new red level by subtracting the first measurement from the red level of the second measurement, a new green level by subtracting the first measurement from the green level of the second measurement, and a new blue level by subtracting the first measurement from the blue level of the second measurement. The new red, green, and blue levels represent the color of the light reflected from the object.

At block 605 of method 600, the color sensing application 111 determines, based on the normalized measurement, one of (i) a presence of bodily exudate or (ii) a volume of bodily exudate present. Processor 206 outputs the color of the object and provides the color to microcontroller 101. The color sensing application 111, executing on microcontroller 101, receives the color value from processor 206 and uses a data structure such as a table to determine a presence of bodily or a value representing a volume of bodily exudate. Microcontroller 101 may store several tables, for example, one table which facilitates the mapping of a color on a color changing indicator such as Bromocresol green, to a pH level, and another table that facilitates the mapping of a color changing indicator to a measure or presence of a volume of bodily exudate.

Additionally, as discussed, color sensing application 111 can perform color calibration. Color sensing application 111 can convert the red, green, and blue levels to hue, saturation, and lightness/value and perform calculations on the hue, saturation, and lightness/value. Color calibration can be implemented via a table. For example, for a given triple of red, green, and blue, adjust the values by certain amount. Color calibration can also be performed in a different domain such as hue, saturation, and lightness, or hue, saturation, and value.

In an aspect, color sensing application 111 can determine the presence of bodily exudate in the presence of movement. For example, sensor package 400 caused to be moved by an infant at the same time as color sensing application 111 is performing measurements. In this case, color sensing application can use a known responsiveness of the absorbent article or color strip at two or more different wavelengths of light to determine a presence of exudate. In an example color sensing application 111 can detect that a response to red light is greater than a response to blue light even in the presence of motion.

In a further aspect, color sensing application 111 can detect when an absorbent article is not attached to an infant. In this case, the sensor responsiveness changes below a threshold, which is detected by color sensing application 111.

Figure 7:
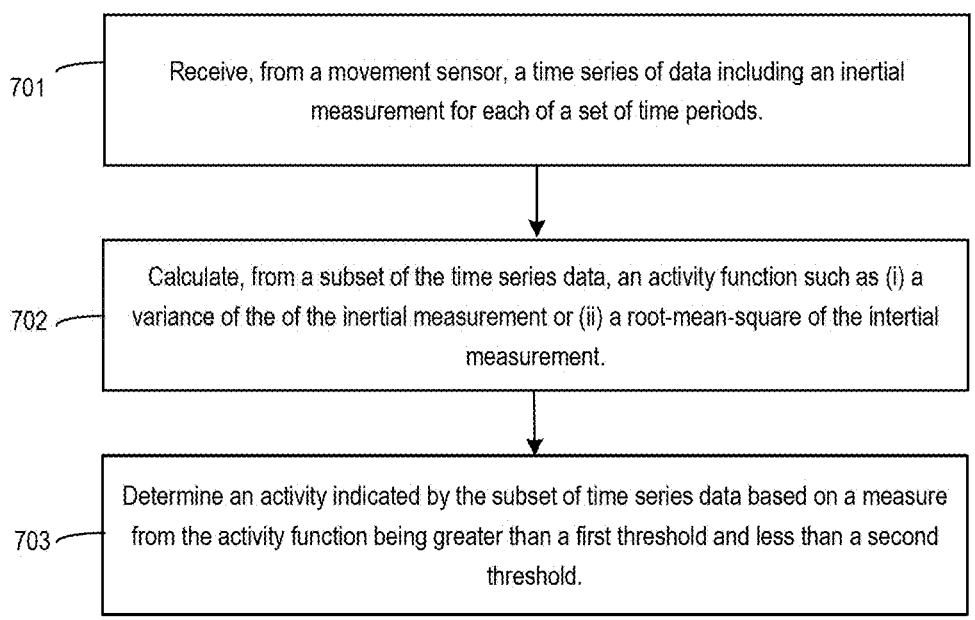
FIG. 7 is a flowchart of an exemplary method used to determine activity from a movement sensor, according to certain aspects of the present disclosure.

FIG. 7 is a flowchart of an exemplary method used to determine activity from a movement sensor, according to certain aspects of the present disclosure. Method 700 can be implemented by activity classification application 116. Further, the operations described with respect to FIG. 7 can be performed by an external device such as a monitor device connected to infant sensing system 100 via a wireless or an external server.

At block 701 of method 700, activity classification application 116 receives, from movement sensor 130, a time series of data including an inertial measurement for each of a set of time periods. Inertial measurements can include acceleration or angular velocity. For example, an accelerometer can provide a triplet of numerical values corresponding to the x, y, and z directions. Activity classification application 116 periodically samples the accelerometer to create a time series of data. Processor 206 annotates each triplet with a timestamp, creating a pair that includes sensor measurement and timestamp. Activity classification application 116 can also sample the gyroscope on a periodic basis. In conjunction with the measurement data from the accelerometer, activity classification application 116 can determine a set of data that includes a gyroscope measurement, e.g. angular velocity, an accelerometer measurement, e.g., a triplet of x-y-z values, and a timestamp.

In an aspect, activity classification application 116 analyzes measurement data in real-time and can update an activity measurement function or the predictive model in real-time. Alternatively, activity classification application 116 can analyze a block of samples at a time. For example, activity classification application 116 can buffer the pairs until a threshold number of pairs have been received and then analyze movement over a window of time.

At block 702 of method 700, activity classification application 116 calculates, from a subset of the time series of data, an activity function from statistical data derived from the inertial measurement. Statistical data can include data such as (i) a statistical variance of the inertial measurement or (ii) a root-mean-square of the inertial measurement. Activity classification application 116 uses an activity measurement function in order to determine activity level. Different measurements of activity can be derived. For example, activity classification application 116 can calculate the statistical variance, standard deviation, or the root mean square (RMS) of the signal. Activity classification application 116 can use another customized metrics based on the accelerometer or gyroscope data. For example, a customized metric that quantifies the level of activity A can be calculated for a given number n of samples with the following function, where Sx, Sy, and Sz are the sum of the square differences from the respective means in the x, y, and z dimensions respectively:

$$A = \sqrt{\frac{(Sx)^2 + (Sy)^2 + (Sz)^2}{n}}$$

At block 703 of method 700, activity classification application 116 determines an activity indicated by the subset of time series data based on a measure from the activity function being greater than a first threshold and less than a second threshold. Activity classification application 116 can determine an activity such as sleeping or awake based on a level of activity being with a range of values. For example, if the activity function measures a level of activity below a first threshold but above zero, then activity classification application 116 determines that the infant is in light sleep. If the activity function measures a level of movement below a second, lower, threshold, then the monitor application determines that the infant is in a deep sleep. Activity classification application 116 can use a state machine to determine activity states.

As discussed, in an aspect, activity classification application 116 can use a predictive model to determine the infant's activity in addition to or instead of algorithms or state machines. Activity classification application 116 provides the accelerometer measurements, the gyroscope measurements, or the output of an activity measurement function to the predictive model. Predictive models discussed herein can be machine learning models such as decision tree classifiers or regression models. Other models are possible.

A predictive model is trained to determine whether a wearer of the sensor is feeding on the left hand side, feeding on the right hand side, sleeping, awake and playing on its back, being held, or sitting. Other detectable activities may include sitting, playing, crawling, walking, etc. Activity classification application 116 can provide data for one or more periods of time to the predictive model. In this manner, predictive model may determine an activity based on present or past activity level.

Figure 8:
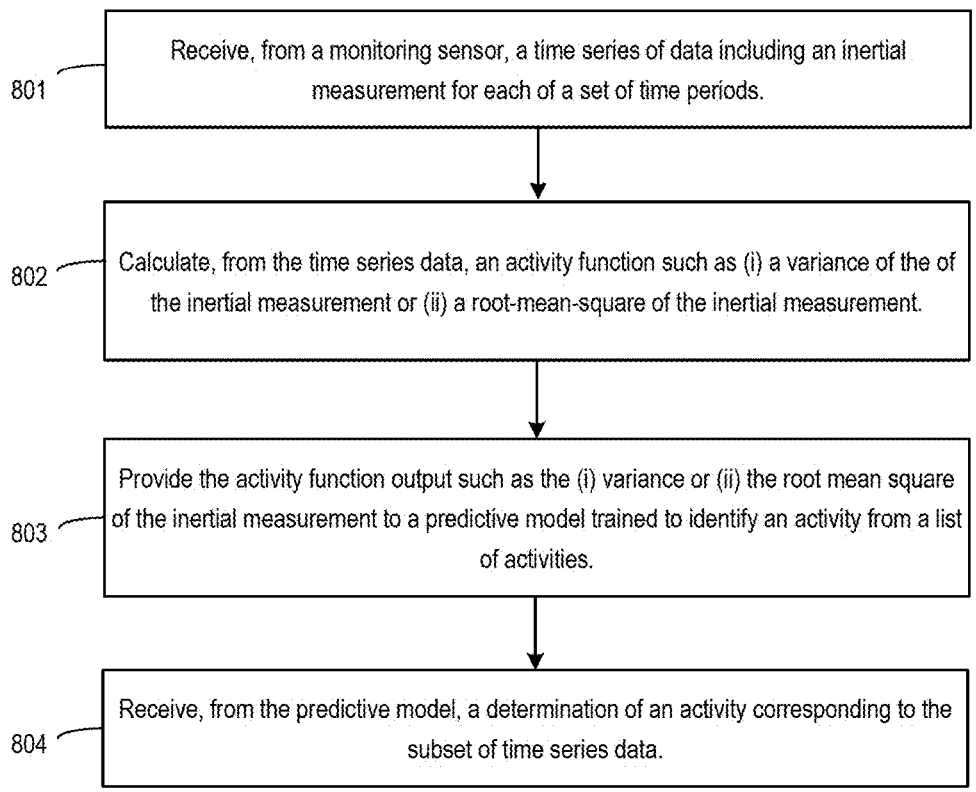
FIG. 8 is a flowchart of an exemplary method used to determine activity from a movement sensor by using a predictive model, according to certain aspects of the present disclosure.

FIG. 8 is a flowchart of an exemplary method used to determine activity from a movement sensor by using a predictive model, according to certain aspects of the present disclosure. Further, the operations described with respect to FIG. 8 can be performed by an external device such as a monitor device connected to infant sensing system 100 via a wireless or an external server.

At block 801 of method 800, activity classification application 116 receives, from a movement sensor, a time series of data including an inertial measurement for each of a set of time periods. At block 801, activity classification application 116 receives the time series of data generally as described with respect to block 701.

At block 802 of method 800, activity classification application 116 calculates, from the time series data, an activity function such as (i) a statistical variance of the of the inertial measurement or (ii) a root-mean-square of the inertial measurement. At block 802, monitor application uses an activity measurement function generally as described with respect to block 702.

At block 803 of method 800, activity classification application 116 provides the activity function the (i) statistical variance or (ii) the root mean square of the inertial measurement to a predictive model trained to identify an activity a list of activities. More specifically, activity classification application 116 provides sensor measurements or the output of the activity function to the predictive model.

The predictive model is trained to determine activity from measurements that indicate movement. The predictive model determines, based on its training, from a predefined set of classes, to which class the activity belongs. An exemplary list of activity classes includes feeding on the left side, feeding on the right side, sleeping, awake but playing on back, being held, and sitting.

Other training classes are possible. For example, the predictive model can be trained to distinguish deep sleep from light sleep, and activities such as crawling, rolling, sitting up, feeding, or nursing from each other. For example, activity classification application 116 may include a predictive model that is trained to distinguish between asleep, awake, stirring, or settled states, and another that is trained to distinguish between light sleep and deep sleep. Training is discussed further with respect to FIG. 9. Stirring represents a state in which an infant is moving more than a first threshold amount and settled represents a state in which the infant has calmed down and is moving less than a second threshold amount.

At block 804 of method 800, activity classification application 116 receives, from the predictive model, a determination of an activity corresponding to the subset of time series data. For example, the predictive model provides a prediction to activity classification application 116 from one of the trained categories such as feeding on the left hand side, feeding on the right hand side, sleeping, awake and playing on its back, being held, or sitting.

Figure 9:
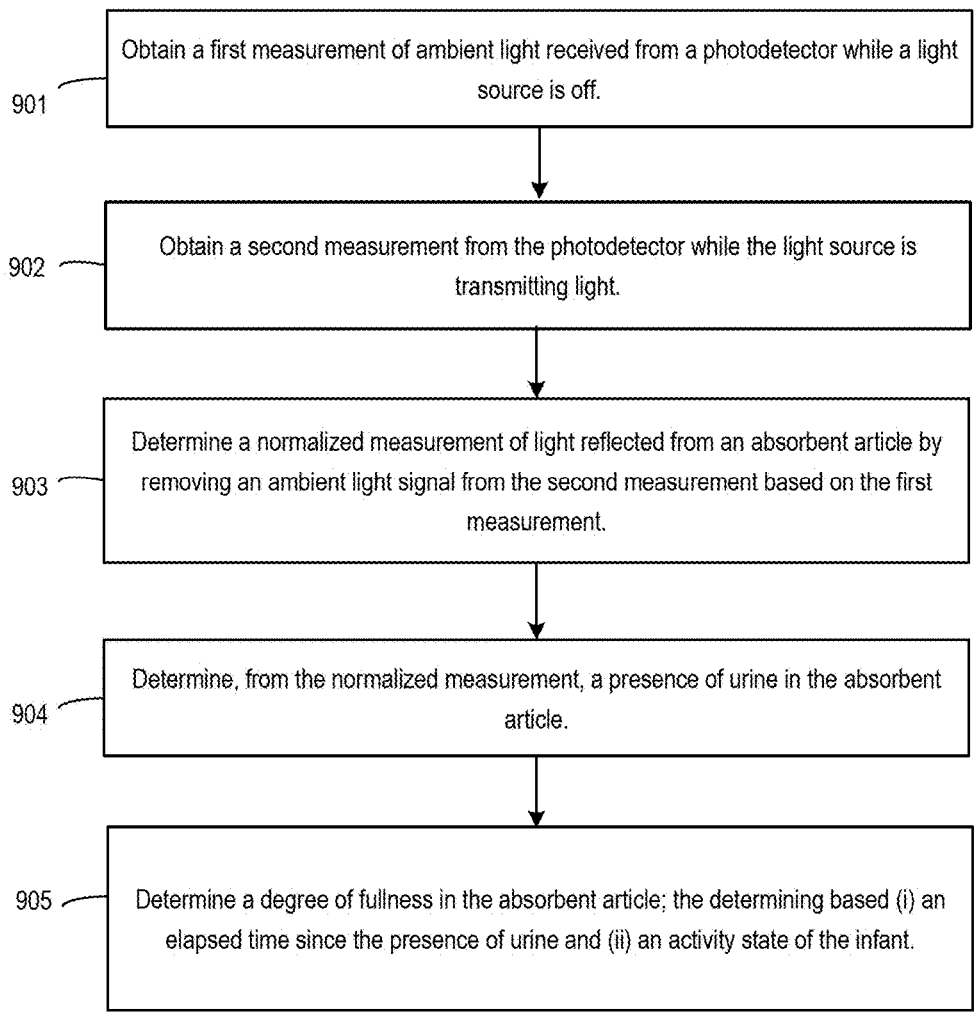
FIG. 9 is a flowchart that describes a method of detecting a volume of bodily exudate in an absorbent article, according to certain aspects of the present disclosure.

FIG. 9 is a flowchart that describes a method 900 of detecting a volume of bodily exudate in an absorbent article, according to certain aspects of the present disclosure.

Method 900 is explained from the perspective of diaper loading application 102, activity classification application 116, and color sensing application 111, but as can be appreciated, different steps of method 900 can be performed by these or other applications. Additionally, one application can perform all of the steps. Further, the operations described with respect to FIG. 9 can be performed by an external device such as a monitor device connected to infant sensing system 100 via a wireless or an external server.

At block 901 of method 900, color sensing application 111 obtains a first measurement of ambient light received from a photodetector while a light source is off. At block 901, color sensing application 111 performs similar functions as described with respect to block 601 of method 600.

At block 902 of method 900, color sensing application 111 obtains a second measurement from the photodetector while the light source is transmitting light. The second measurement includes a measurement of the ambient light and the transmitted light reflected from an absorbent article. At block 902, color sensing application 111 performs similar functions as described with respect to blocks 601-602 of method 600.

At block 903 of method 900, diaper loading application 115 determines a normalized measurement of the light reflected from an absorbent article by removing an ambient light signal from the second measurement based on the first measurement. At block 903, color sensing application 111 performs similar functions as described with respect to block 604 of method 600.

At block 904 of method 900, diaper loading application 115 determines, from the normalized measurement, a presence of urine in the absorbent article. At block 904, diaper loading application 115 causes color sensing application 111 to perform similar functions as described with respect to block 605 of method 600.

At block 905 of method 900, diaper loading application 115 determines a degree of fullness of the absorbent article. The degree of fullness reflects an amount of storage space in an absorbent article that is filled or has absorbed bodily exudate relative to a total amount of storage space that can be filled with bodily exudate. In some cases, the degree of fullness of the absorbent article is derived from a volume of urine present in the diaper. The volume can be determined using different inputs such as (i) an elapsed time since the presence of urine, (ii) when the diaper was changed, and (iii) a state of the infant (e.g., awake or sleeping).

A diaper replacement can be indicated by a caregiver, e.g., via a user interface or other input to the infant sensing system. Alternatively, diaper loading application 115 can detect a presence of a new diaper by detecting a removal of the sensor from the infant's diaper, or a decrease in or absence of wetness measured.

Understanding the amount of time in asleep and/or awake states facilitates improved predictions. For example, infants may urinate at a slower frequency and quantity during the night relative to the day. Additionally, with more accurate predictions in this respect, the infant sensing system has an added benefit of allowing a caregiver to sleep longer if a diaper change is not imminently necessary. As explained with respect to FIGS. 7-8, a movement sensor in conjunction with a predictive or state model can be used by activity classification application 116 to determine whether an infant is asleep, awake, resting, etc. hence, at block 905, example operations include operations performed in methods 700 and/or 800.

Additionally, in some cases, the diaper loading application 115 receives an input about the particular type, brand, or size (e.g., standard sizes such as 1, 2, 3. etc.) of diaper being used or whether the diaper is a regular (daytime) diaper or an overnight diaper. Overnight diapers may have a greater absorption capacity. Further, diaper loading application 115 can receive demographic information about the infant such as age, gender, weight, etc., which can be used for the basis of predictions. For example, larger infants may urinate more, resulting in a diaper needing to be replaced sooner than with a smaller infant.

Diaper loading application 115 can also determine a time until the absorbent article is full. For example, diaper loading application 115 access a capacity of the diaper (e.g., a volume of liquid that can theoretically be stored in the diaper), calculate a rate of volume increase (e.g., based on frequency and amount if urine events since the diaper was replaced) and calculate a time at which the diaper will be full. Diaper loading application 115 can cause infant sensing system 100 to send an alert on or before the time to remind a caregiver to tend to the infant.

Statistical methods can be used. For example, diaper loading application 115 can create a function that outputs a volume of urine based on several inputs. Examples of inputs can be (1) when the diaper was replaced with a new one (e.g., how long the current diaper has been on an infant), (2) whether the diaper is wet (or when it first turned wet), (3) the amount of time spent in asleep or awake states since the diaper became wet, or (4) other data such as diaper type. Diaper loading application 115 can solve the function with one or more regression models (e.g., linear, quadratic, etc.) or machine learning models (e.g., a decision tree classifier or other classification model). By solving the model, diaper loading application 115 determines a volume of urine present in the diaper.

FIG. 10 is a diagram depicting an example computing system for performing functions related to color detection and detection of bodily exudate, according to some aspects of the present disclosure. Some or all of the components of the computing system 1000 can belong to microcontroller 101 or the processor 206 of FIG. 1. For example, the color sensing application 111 may operate on the computing system 1000. The computing system 1000 includes one or more processors 1002 communicatively coupled to one or more memory devices 1014. The processor 1002 executes computer-executable program code, which can be in the form of non-transitory computer-executable instructions, stored in the memory device 1014, accesses information stored in the memory device 1014, or both. Examples of the processor 1002 include a microprocessor, an application-specific integrated circuit ("ASIC"), a field-programmable gate array ("FPGA"), or any other suitable processing device. The processor 1002 can include any number of processing devices, including one.

The memory device 1014 includes any suitable computer-readable medium such as electronic, optical, magnetic, or other storage device capable of providing a processor with computer-readable instructions or other program code. Non-limiting examples of a computer-readable medium include a magnetic disk, a memory chip, a ROM, a RAM, an ASIC, optical storage, magnetic tape or other magnetic storage, or any other medium from which a processing device can read instructions. The instructions may include processor-specific instructions generated by a compiler or an interpreter from code written in any suitable computer-programming language, including, for example, C, C++, C#, Visual Basic, Java, Python, Perl, JavaScript, and ActionScript.

The computing system 1000 may also include a number of external or internal devices such as input or output devices. For example, the computing system 1000 is shown with an input/output ("I/O") interface 1008 that can receive input from input devices or provide output to output devices. A bus 1006 can also be included in the computing system 1000. The bus 1006 can communicatively couple one or more components of the computing system 1000 and allow for communication between such components.

The computing system 1000 executes program code that configures the processor 1002 to perform one or more of the operations described above with respect to FIGS. 1-5. The program code of the color sensing application 111, diaper loading application 115, or activity classification application 116, which can be in the form of non-transitory computer-executable instructions, can be resident in the memory device 1014 or any suitable computer-readable medium and can be executed by the processor 1002 or any other one or more suitable processor. Execution of such program code configures or causes the processor(s) to perform the operations described herein with respect to the microcontroller 101. In additional or alternative aspects, the program code described above can be stored in one or more memory devices accessible by the computing system 1000 from a remote storage device via a data network. The microcontroller 101 and any processes can use the memory device 1014. The memory device 1014 can store, for example, additional programs, or data used by the applications executing on the processor 1002 such as the color sensing application 111.

The computing system 1000 can also include at least one network interface 1004. The network interface 1004 includes any device or group of devices suitable for establishing a wired or wireless data connection to one or more data networks. Non-limiting examples of the network interface 1004 include an Ethernet network adapter, WiFi network, Bluetooth, or Bluetooth Low Energy (BLE), a modem, or the like. The computing system 1000 is able to communicate with one or more other computing devices or computer-readable data sources via a data network using the network interface 1004.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multi-purpose microprocessor-based computer systems accessing stored software that programs or configures the computing system from a general purpose computing apparatus to a specialized computing apparatus implementing one or more aspects of the present subject matter. Any suitable programming, scripting, or other type of language or combinations of languages may be used to implement the teachings contained herein in software to be used in programming or configuring a computing device.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

That which is claimed is:

1. A method for predicting a loading of an absorbent article, the method comprising:
   obtaining a first measurement of ambient light received from a photodetector while a light source is off;
   obtaining a second measurement from the photodetector while the light source is transmitting light, the second measurement comprising a measurement of the ambient light and the transmitted light reflected from the absorbent article;
   determining a normalized measurement of light reflected from an absorbent article by removing an ambient light signal from the second measurement based on the first measurement of ambient light;
   determining, from the normalized measurement of light, a presence of urine in the absorbent article;
   determining, from a time series of data including an inertial measurement for each of a set of time periods, an activity state of an infant wearing the absorbent article; and
   determining a degree of fullness of the absorbent article, wherein the determining is based on (i) an elapsed time since the determination of the presence of urine and (ii) the activity state.

2. The method of claim 1, further comprising determining, based on the degree of fullness, that the absorbent article should be replaced.

3. The method of claim 1, wherein determining the degree of fullness is based on a size of the absorbent article.

4. The method of claim 1, wherein determining the degree of fullness comprises using one or more of (i) a regression model or (ii) a machine learning model to solve a function based on the elapsed time and the activity state.

5. The method of claim 1, wherein determining the degree of fullness is further based on (iii) an additional elapsed time since the absorbent article was placed on the infant.

6. The method of claim 1, wherein the activity state comprises one of asleep or awake.

7. The method of claim 1, further comprising accessing a set of demographics about the infant, and wherein determining the degree of fullness is based in part on the set of demographics.

8. The method of claim 1, further comprising accessing a type of the absorbent article, wherein the type is one of a nighttime diaper or a daytime diaper, and wherein determining the degree of fullness is based in part on the type.

9. The method of claim 1, wherein determining the activity state of the infant comprises:
   receiving, from a movement sensor, a plurality of inertial measurements in three dimensions for a time period;
   calculating statistical data derived from the plurality of inertial measurements;
   providing the plurality of inertial measurements and the statistical data to a predictive model; and
   receiving, from the predictive model and based on the plurality of inertial measurements, the activity state.

10. The method of claim 1, wherein the second measurement comprises separate measurements of red light, green light, and blue light, wherein determining the normalized measurement of light comprises determining a separate intensity of red light, green light, and blue light, and wherein determining the degree of fullness is based on the separate intensities of the red, green, and blue lights.

11. The method of claim 1, wherein the light source is configured to transmit light at a particular wavelength that is determined based on a responsiveness of the absorbent article to different wavelengths of light.

12. The method of claim 1, wherein the absorbent article comprises a printed or coated region comprising a color changing indicator.

13. The method of claim 1, further comprising:
retrieving, from a memory, a stored color calibration value; and
determining, based on the normalized measurement of light and the stored color calibration value, a color of the absorbent article, wherein the stored color calibration value is determined using a white colored object and the determining the color comprises white level correction.

14. A system for determining a volume of bodily exudate in an absorbent article, the system comprising:
a light source;
a photodetector;
a movement sensor; and
a processor that is configured to:
obtain a first measurement of ambient light received from the photodetector while the light source is off;
obtain a second measurement from the photodetector while the light source is transmitting light, the second measurement comprising a measurement of the ambient light and the transmitted light reflected from the absorbent article;
determine a normalized measurement of light reflected from the absorbent article by removing an ambient light signal from the second measurement based on the first measurement of ambient light;
obtain, from the movement sensor, a time series of data including an inertial measurement for each of a set of time periods;
determine, using at least one of (i) the normalized measurement of light or (ii) the time series of data; a degree of fullness of the absorbent article, the determining comprising calculating a time until the absorbent article is expected to be full by using a regression model to solve a function based on:
an elapsed time since a detection of a presence of urine, and
an activity state of an infant wearing the absorbent article, wherein the activity state is determined from the time series of data.

15. The system of claim 14, wherein determining the degree of fullness is performed by an external device.

16. The system of claim 14, wherein determining the degree of fullness is further based on (iii) an additional elapsed time since the absorbent article was placed on the infant.

17. A system comprising:
a non-transitory computer-readable medium storing computer-executable instructions; and
a processing device communicatively coupled to the non-transitory computer-readable medium for executing the computer-executable instructions, wherein executing the computer-executable instructions configures the processing device to perform operations comprising:
obtaining a first measurement of ambient light received from a photodetector while a light source is off;
obtaining a second measurement from the photodetector while the light source is transmitting light, the second measurement comprising a measurement of the ambient light and the transmitted light reflected from an absorbent article;
determining a normalized measurement of light reflected from the absorbent article by removing an ambient light signal from the second measurement based on the first measurement of ambient light;
determining, from the normalized measurement of light, a presence of urine in the absorbent article;
determining a degree of fullness of the absorbent article based on (i) an elapsed time since the presence of urine and (ii) an activity state of an infant wearing the absorbent article;
determining, from the degree of fullness of the absorbent article, that the absorbent article should be replaced; and responsive to determining that the absorbent article should be replaced, causing an alert to be generated.

18. The system of claim 17, wherein determining the degree of fullness of the absorbent article comprises using one or more of (i) a regression model or (ii) a machine learning model to solve a function based on the elapsed time and the activity state.

19. The system of claim 17, wherein the activity state is determined by:
receiving, from a movement sensor, a plurality of inertial measurements in three dimensions for a time period;
calculating statistical data derived from the plurality of inertial measurements;
providing the plurality of inertial measurements and the statistical data to a predictive model; and
receiving, from the predictive model and based on the plurality of inertial measurements, the activity state.

20. The system of claim 17, wherein the light source is configured to transmit light at a particular wavelength that is determined based on a responsiveness of the absorbent article to different wavelengths of light.

* * * * *